US00PP07985P

United States Patent [19]

VandenBerg

[11] Patent Number: Plant 7,985

[45] Date of Patent: Sep. 22, 1992

[54] CHRYSANTHEMUM PLANT NAMED BLUSH

[75] Inventor: Cornelis P. VandenBerg, Salinas, Calif.

[73] Assignee: Yoder Brothers, Inc., Barberton, Ohio

[21] Appl. No.: 651,005

[22] Filed: Feb. 5, 1991

[51] Int. Cl.[5] ..... A01H 5/00

[52] U.S. Cl. ..... Plt./82.4

[58] Field of Search ..... Plt./74

*Primary Examiner*—James R. Feyrer

*Attorney, Agent, or Firm*—Foley & Lardner

[57] ABSTRACT

A Chrysanthemum plant named Blush particularly characterized by its flat capitulum form; daisy capitulum type; soft pink ray floret color; diameter across face of capitulum of 127 to 140 mm when fully opened when grown as a pinched disbudded pot mum; photoperiodic dresponse to short days of 47 to 55 days; plant height of 23 to 28 cm when grown as a pinched pot mum with 15 to 22 long days prior to start of short days and 1 to 3 applications of 2500 ppm B-9 SP; semi-spreading branching pattern, with 4 to 5 breaks per plant after pinch; and recommended as disbud pot mum.

3 Drawing Sheets

The present invention comprises a new and distinct cultivar of Chrysanthemum, botanically known as *Dendranthema grandiflora*, and referred to by the cultivar name Blush.

Blush, identified as 4384 (86-627002), was originated from a cross made by Cornelis P. VandenBerg in a controlled breeding program in Salinas, Calif., in 1986.

Blush was the result of a controlled selfing of the parent identified as 5502 (83-436012), an unnamed seedling described as a white flat disbud daisy pot mum and having a flowering response to short days of 50 to 59 days under normal conditions, a height of 20 to 28 cm with 15 to 16 long days after stick and 1 to 3 applications of 2500 ppm B-9 SP when grown as a pinched pot mum, semi-spreading branching habit with 3 to 4 laterals after pinch, and a diameter of capitulum of 108 to 114 mm.

Blush was discovered ans selected as one flowering plant within the progeny of the stated selfing by Cornelis P. VandenBerg in December of 1986, in a controlled environment in Salinas, Calif.

The first act of asexual reproduction of Blush was accomplished when vegetative cuttings were taken from the initial selection in Feb. 1987 in a controlled environment in Salinas, Calif., by technicians working under supervision of Cornelis P. VandenBerg.

Horticultural examination of controlled flowerings of successive plantings has shown that the unique combination of characteristics as herein disclosed for Blush are firmly fixed and are retained through successive generations of asexual reproduction.

Blush has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Blush, which, in combination, distinguish this Chrysanthemum as a new and distinct cultivar:

1. Flat capitulum form.
2. Daisy capitulum type.

3. Soft pink ray floret color.
4. Diameter across face of capitulum of 127 to 140 mm when fully opened, when grown as a pinched disbudded pot mum.
5. Photoperiodic flowering response to short days of 47 to 55 days.
6. Plant height, with 15 to 22 long days after sticking unrooted cuttings, and with 1 to 3 applications of 2500 ppm B-9 SP, ranging from 23 to 28 cm when grown as a pinched pot mum with 4 cuttings in a 15 cm pot.
7. Branching pattern is semi-spreading, each plant having 4 to 5 laterals after pinch.
8. Recommended as a disbud pot mum.

The accompanying photographic drawings show typical inflorescence and leaf characteristics of Blush, with the colors being as nearly true as possible with illustrations of this type.

Sheet 1 is a color photograph of Blush grown as a pinched spray pot mum with 4 cuttings in a 15 cm pot.

Sheet 2 is a black and white photograph of three views of the inflorescence of Blush.

Sheet 3 is a black and white photograph showing the upper and under sides of the leaves of Blush at 3 stages of development (mature, intermediate and immature).

In sheets 2 and 3 a measuring tape in centimeters has been included.

of the commercial cultivars known to the inventor, the most similar in comparison to Blush is the cultivar Splendor, disclosed in U.S. Plant Pat. No. 5,225. Reference is made to attached Chart A, which compares certain characteristics of Blush to the same characteristics of Splendor.

Similar traits are capitulum form and type, plant height, number of laterals after pinch and recommended use as a disbud pot mum. Blush has a lighter ray floret color than Splendor, has a slightly smaller diameter of capitulum, a much shorter flowering response to short days, and a more spreading branching pattern. In addition, Blush has a flatter flower form and fewer ray florets.

When compared with the parent, Blush has a larger diameter of capitulum, a faster flowering response to short days, and an average of one more lateral after pinch. In addition, Blush has a soft pink ray floret color, with the ray floret color of the parent being clear white.

In the following description color references are made to The Royal Horticultural Society Colour Chart. The color values were determined on plant material grown as a pinched disbudded pot mum in Salinas, Calif. on Nov. 26, 1990.

Classification:

*Botanical.—Dendranthema grandiflora* cv Blush.

*Commercial.*—Daisy disbud pot mum.

Inflorescence

A. Capitulum:

*Form.*—Flat.

*Type.*—Daisy.

Diameter across face.—127 to 140 mm when fully opened.

B. Corolla of ray florets:

*Color (general tonality from a distance of three meters).*—Soft pink.

*Color (upper surface).*—75B to 75C, slightly streaked.

*Color (under surface).*—75D.

*Shape.*—Straight, pointed, slightly ribbed.

C. Corolla of disc florets:

*Color (mature).*—7B.

*Color (immature).*—144A to 144B.

D. Reproductive organs:

*Androecium.*—Present on disc florets only; scant pollen.

*Gynoecium.*—Present on both ray and disc florset.

Plant

A. General Appearance:

*Height.*—23 to 28 cm when grown as a pinched pot mum in a 15 cm pot with 15 to 22 long days after direct sticking of unrooted cuttings and 1 to 3 applications of 2500 ppm B-9 SP.

Branching pattern.—Semi-spreading, with 4 to 5 laterals after pinch.

B. Foliage:

*Color (upper surface).*—147A.

*Color (under surface).*—147B.

*Shape.*—See photograph.

t,0070

I claim:

1. A new and distinct Chrysanthemum plant named Blush, as described and illustrated.

* * * * *

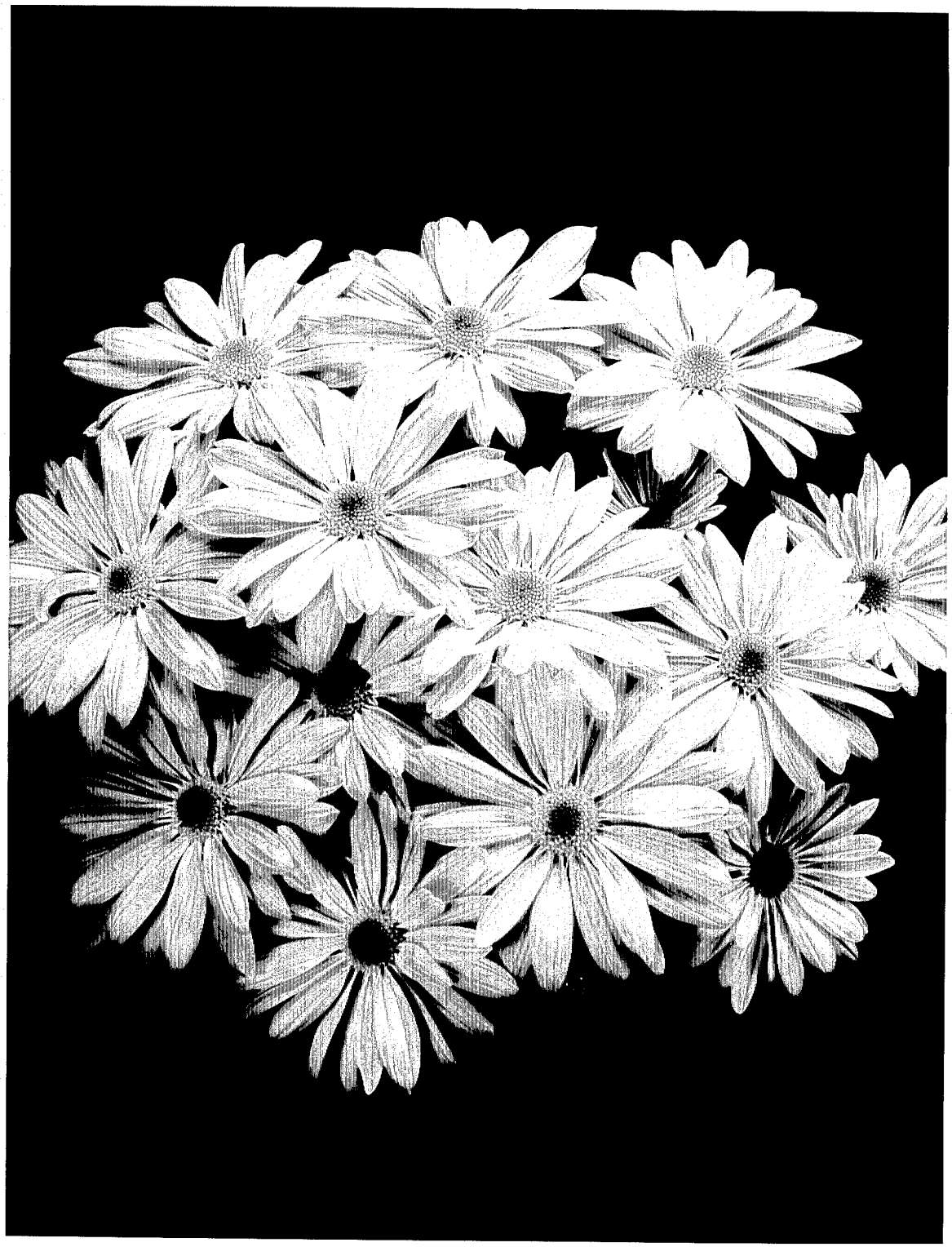

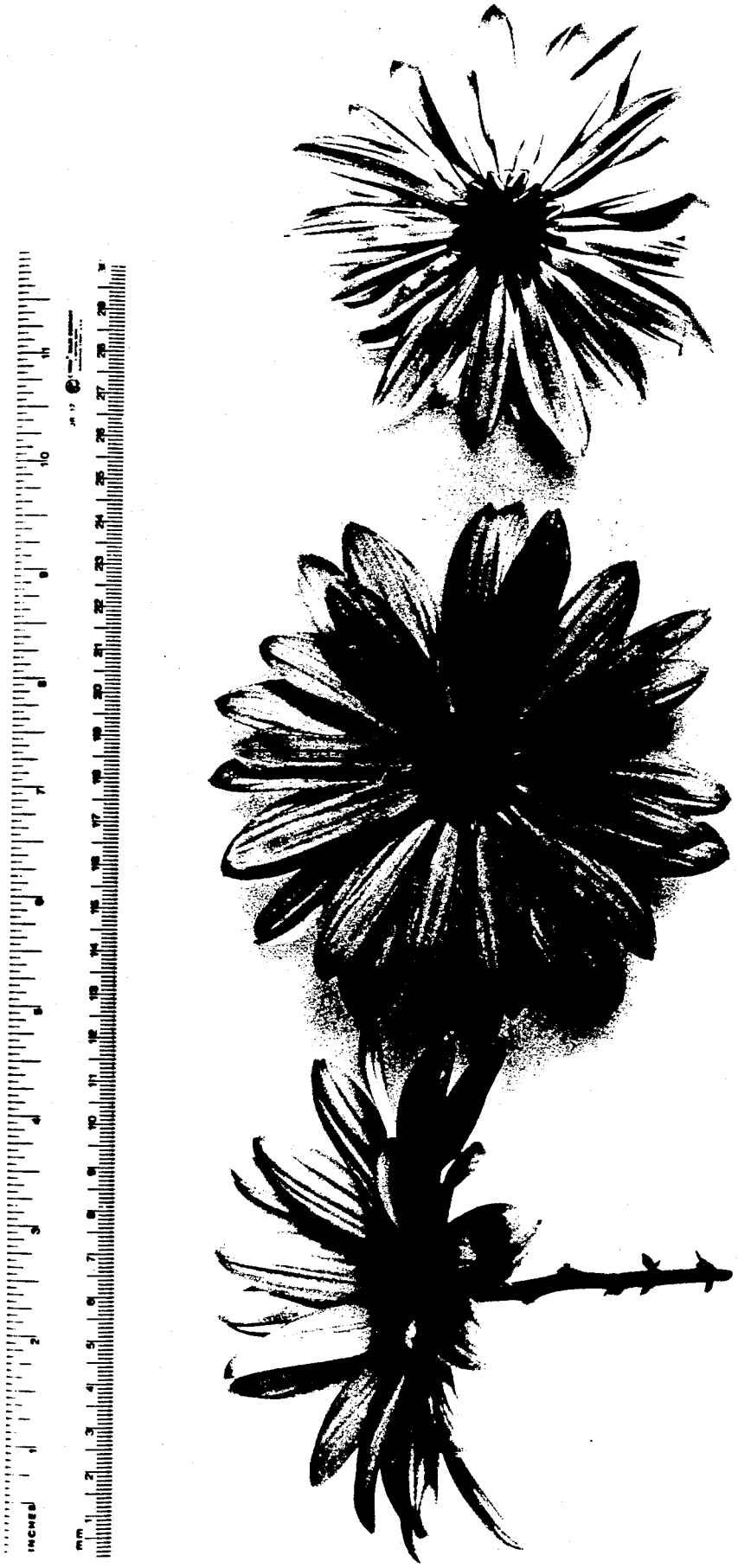

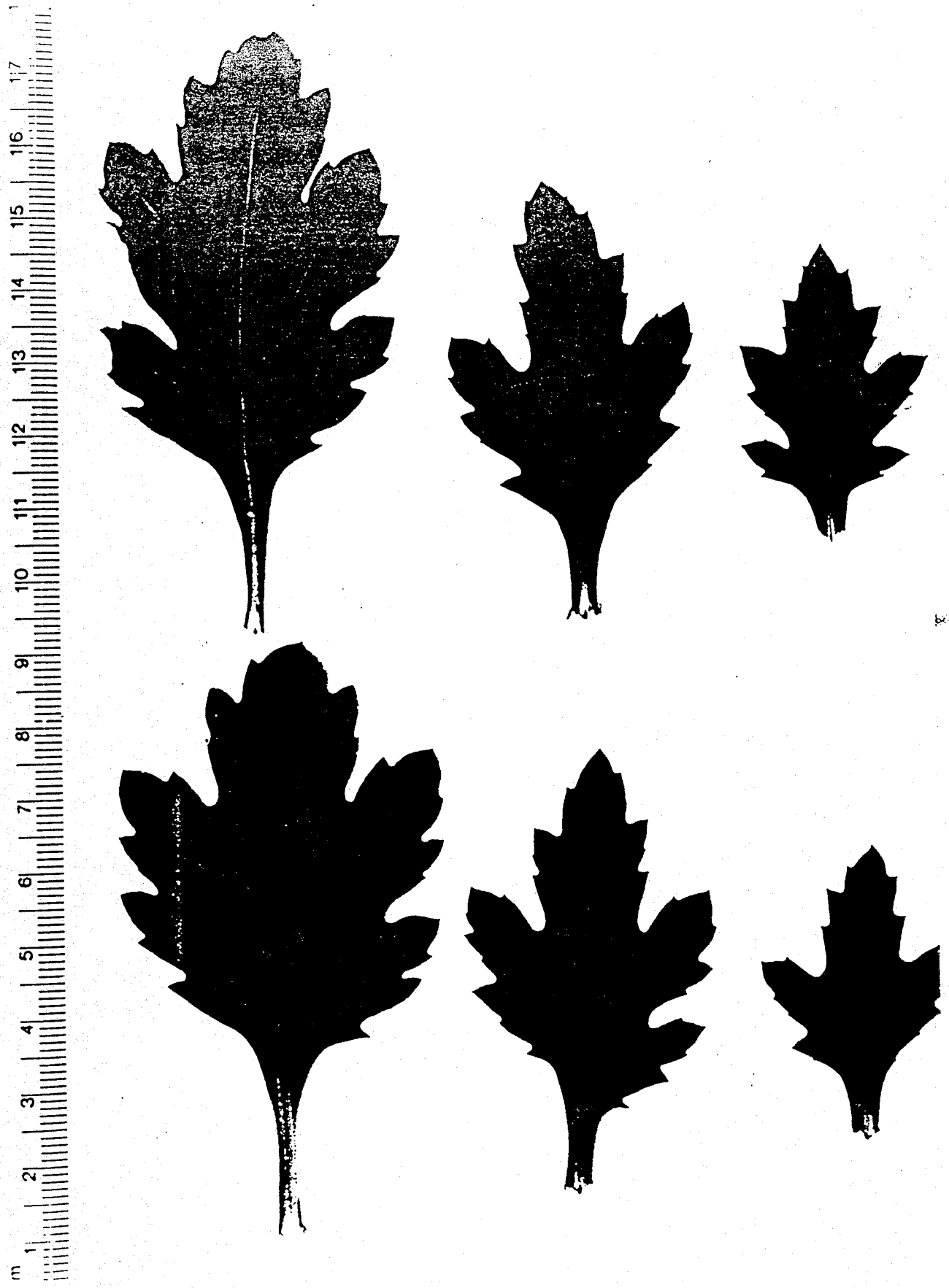
m
1
2
3
4
5
6
7
8
9
10
11
12
13
14
15
16
17

UNITED STATES PATENT AND TRADEMARK OFFICE

CERTIFICATE OF CORRECTION

PATENT NO. : PP 7,985

DATED : September 22, 1992

INVENTOR(S) : Cornelis P. Vandenberg

It is certified that error appears in the above-indentified patent and that said Letters Patent is hereby corrected as shown below:

Column 4, below line 19, and above the single patent claim, insert Chart A, as attached.

Column 4, line 20, "t,0070" should be deleted.

Signed and Sealed this

Twelfth Day of July, 1994

Bruce Lehman

*Attest:*

BRUCE LEHMAN

*Attesting Officer*

*Commissioner of Patents and Trademarks*

CHART A

COMPARISON OF BLUSH AND SPLENDOR

| Characteristic | Blush | Splendor |
|---|---|---|
| Ray floret color | Soft pink | Light lavender |
| Capitulum form and type | Flat daisy | Flat daisy |
| Diameter across face of capitulum | 127 to 140 mm | 145 to 160 mm |
| Flowering response | 47 to 55 days | 54 to 60 days |
| Plant height with 15 to 22 long days | 23 to 28 cm | 23 to 30 cm |
| Branching pattern | Semi-spreading | Upright |
| | 4 to 5 laterals | 4 to 5 laterals |
| Recommended as | Disbud pot mum | Disbud pot mum |

COMPARISONS MADE OF PLANTS GROWN AS
PINCHED DISBUDDED POT MUMS IN
SALINAS, CALIFORNIA